United States Patent
Ricke et al.

(10) Patent No.: US 10,410,837 B2
(45) Date of Patent: Sep. 10, 2019

(54) PLASMA-TREATMENT INSTRUMENT

(71) Applicant: CINOGY GmbH, Duderstadt (DE)

(72) Inventors: Melanie Ricke, Katlenburg-Lindau (DE); Dirk Wandke, Heilbad Heiligenstadt (DE); Leonhard Trutwig, Duderstadt (DE); Karl-Otto Storck, Duderstadt (DE); Mirko Hahnl, Berlingerode (DE)

(73) Assignee: CINOGY GMBH, Duderstadt (DE)

( * ) Notice: Subject to any disclaimer, the term of this patent is extended or adjusted under 35 U.S.C. 154(b) by 0 days.

(21) Appl. No.: 16/214,584

(22) Filed: Dec. 10, 2018

(65) Prior Publication Data

US 2019/0180987 A1 Jun. 13, 2019

(30) Foreign Application Priority Data

Dec. 13, 2017 (DE) .......................... 10 2017 129 718

(51) Int. Cl.
*H01J 37/32* (2006.01)
*H05H 1/24* (2006.01)
(Continued)

(52) U.S. Cl.
CPC ........ *H01J 37/32348* (2013.01); *A61N 1/328* (2013.01); *H01J 37/3277* (2013.01); *H05H 1/2406* (2013.01); *H05H 1/34* (2013.01); *H05H 1/46* (2013.01); *H05H 2001/2412* (2013.01); *H05H 2001/2418* (2013.01); *H05H 2245/123* (2013.01)

(58) Field of Classification Search
CPC .. H01J 37/32348; H01J 37/3277; H05H 1/46; H05H 1/34; H05H 1/2406; H05H 2245/123; H05H 2001/2412; H05H 2001/2418; A61N 1/328
See application file for complete search history.

(56) References Cited

U.S. PATENT DOCUMENTS 9,756,712 B2 * 9/2017 Wandke .................... A61L 2/14
10,143,861 B2 * 12/2018 Slayton .................. A61B 18/18
(Continued)

FOREIGN PATENT DOCUMENTS

DE  10 2015 108 884 A1  12/2016
EP       2 946 641 B1  11/2015
(Continued)

*Primary Examiner* — Tracie Y Green
(74) *Attorney, Agent, or Firm* — W&C IP (57) ABSTRACT

A plasma-treatment instrument for treating a surface with a dielectric-barrier plasma field generated between an electrode and the surface has a high a.c. voltage supplied to the electrode by a controller. The electrode forms with a dielectric surrounding the electrode a cylindrical roller that is rotatably supported in a grip housing. The plasma-treatment instrument has a shell surface and is capable of being rolled along the surface. The plasma-treatment allows an efficient and safe treatment of the surface by virtue of the fact that the electrode includes at least two partial electrodes arranged alongside one another at equal intervals from the shell surface and which are insulated from one another by the dielectric. The at least two partial electrodes are connected to different terminals of a source of high a.c. voltage.

4 Claims, 6 Drawing Sheets

(51) Int. Cl.
*A61N 1/32* (2006.01)
*H05H 1/34* (2006.01)
*H05H 1/46* (2006.01)

(56) References Cited

U.S. PATENT DOCUMENTS

2015/0157870 A1 6/2015 Kalghatgi et al.
2015/0357163 A1* 12/2015 Trutwig .................... A61L 2/14
 313/48
2019/0014651 A1* 1/2019 Trutwig ................ A61L 2/0029

FOREIGN PATENT DOCUMENTS

| WO | 2013/156352 A2 | 10/2013 |
| WO | 2016/193406 A1 | 12/2016 |
| WO | 2017/190724 A1 | 11/2017 |

\* cited by examiner

PLASMA-TREATMENT INSTRUMENT

FIELD OF THE INVENTION

The invention relates to a plasma-treatment instrument for treating a surface with a dielectric-barrier plasma field which is generated between an electrode, supplied with a high a.c. voltage by a control device, and the surface, wherein the electrode forms with a dielectric surrounding the electrode a cylindrical roller, supported rotatably in a grip housing, with a shell surface which is capable of being rolled on the surface.

BACKGROUND

A plasma-treatment instrument of such a type is known through EP 2 946 641 B1. The cylindrical roller is rotatably supported in the grip housing by two end-pieces. The electrode extends as a cylindrical hollow electrode over the axial length of the roller and is screened off toward the shell surface of the roller by the dielectric. The dielectric in this case exhibits a structuring, by virtue of which air spaces are formed on the shell surface of the roller when the roller is rolled on the surface to be treated, in particular on the skin surface or wound surface of a living being that is to be treated for cosmetic or therapeutic purposes. The electrode and the dielectric may have been designed to be flexible, so that the roller can, to a certain extent, adapt itself to irregularities of the surface to be treated, so that a controlled plasma treatment—such as is needed, in particular, for the treatment of the skin surface of a living being—is made possible that can be managed in metered manner. In the known arrangement, the roller exhibits a single electrode, to which a high a.c. voltage is capable of being connected through the grip housing. The surface to be treated, in particular the skin surface of a living being, acts in this case as reference electrode or ground electrode.

SUMMARY

The object underlying the present invention is to create a structural design of the treatment instrument with which an improvement of the efficiency and/or of the variability of the treatment instrument is made possible.

For the purpose of achieving this object, in accordance with the invention a plasma-treatment instrument of the aforementioned type is characterized in that the electrode consists of at least two partial electrodes arranged alongside one another at the same spacing from the shell surface and insulated from one another by the dielectric, which are connected to different terminals of a source of high a.c. voltage.

The plasma-treatment instrument according to the invention consequently exhibits an electrode arrangement in which partial electrodes are arranged alongside one another on the shell surface in alternating manner. The partial electrodes are connected to different terminals of the source of high a.c. voltage.

In this case, one partial electrode can have a high a.c. voltage signal applied to it, whereas the other partial electrode is at a reference potential (in general, ground potential). In this case, the plasma field forms between the two electrodes with a curved marginal region which is available for the formation of plasma. The electrode arrangement consequently defines the reference potential.

In another, preferred embodiment, adjacent partial electrodes are fed by the control device with equal-but-opposite—with respect to the waveform and the voltage level—partial a.c. voltages compensating each other. This arrangement has the advantage that the field forming between the partial electrodes has a field intensity that is twice as high, because the potential difference between the peak values formed in relation to a reference potential is, by reason of the sign inversion, twice as great as in relation to the reference potential. In addition, the advantage arises that the fields that are active for the formation of plasma are twice as intense in the near region of the electrode as in relation to the reference potential but cancel each other out in the somewhat more remote region, since they are equal but opposite. In this way, although a large active field is provided for the formation of the plasma in the immediate vicinity of the electrodes, a practically field-free space is established at a certain spacing, since the fields annihilate each other in relation to the reference potential that is constituted by the surface to be treated.

In particular for the last-named effect, it is an advantage if the partial electrodes exhibit strip-like sections which are arranged alongside one another on the shell surface of the roller, extending parallel to one another. These sections preferably extend in the axial direction on the shell surface. However, it is also possible to make the strip-like sections of the partial electrodes extend in the circumferential direction, so that they form annular sections on the shell surface, which adjoin one another in alternating manner in the axial direction.

Preferred is an embodiment in which the partial electrodes from different axial marginal sections are arranged in alternating manner relative to one another in the circumferential direction with sections extending axially in comb-like manner, and are insulated from one another by a meandering dielectric strip.

Such designs of the partial electrodes can be produced, for instance, by flexible metallic foils. Preferably, however, the partial electrodes consist of a castable synthetic material such as, in particular, silicone, which has been made conductive by means of conducting additives. The dielectric may preferentially have been formed from the same or related synthetic material without the conducting additives. In this way, the dielectric and the electrode enter into a direct materially closed connection without the addition of adhesives.

In the preferred embodiment, in which the sections of the partial electrodes extend in the axial direction, numerous sections of the partial electrodes adjoin one another in alternating manner, viewed in the circumferential direction of the shell surface. The number of sections is preferentially ≥6, more preferably ≥8, and in particular ≥10.

The diameter of the roller preferably amounts to between 10 mm and 50 mm, more preferably between 15 mm and 25 mm.

For the purpose of making a uniform plasma field possible on the shell surface, the dielectric has preferably been provided with elevations which act as spacing elements between the surface to be treated and the continuous dielectric layer covering the electrode, and, when applied to the surface to be treated, exhibit air spaces between themselves, in which the plasma is able to form. The height of the elevations is preferably between 0.5 mm and 20 mm, more preferably between 1 mm and 10 mm, in particular between 1 mm and 5 mm. In another embodiment, the elevations may also form a lattice structure consisting of intersecting ribs, preferentially of equal height.

The peak voltage of the high a.c. voltage being used may expediently lie between ±10 kV and ±100 kV. The alternating frequencies of the high a.c. voltages expediently lie between a few 100 Hz and approximately 100 MHz.

The high a.c. voltage can, in particular, also be generated in pulse form. The control device in this case can generate individual trigger pulses, for instance, between which a pause-time lies which is long in comparison with the half-width of the trigger pulses. The trigger pulses can arrive at a coil arrangement for generating the high-voltage pulses, as a result of which a short pulse train with strongly falling pulse amplitudes forms by reason of oscillation processes. For the generation of equal-but-opposite pulse trains, two identical coil arrangements are provided which are driven at the same time with trigger pulses of differing polarity, so that the equal-but-opposite pulse trains result.

In practice, it may happen that the identity of the equal-but-opposite pulse trains only obtains approximately, so that a constant cumulative potential, formed from the equal-but-opposite signals, in the sense of the invention obtains even when the cumulative potential is still subject to slight fluctuations of, for instance, less than 5% of the peak voltage.

DESCRIPTION OF THE DRAWINGS

The invention will be elucidated in more detail in the following with reference to an embodiment represented in the drawings. Shown are.

DETAILED DESCRIPTION

Figure 1A:
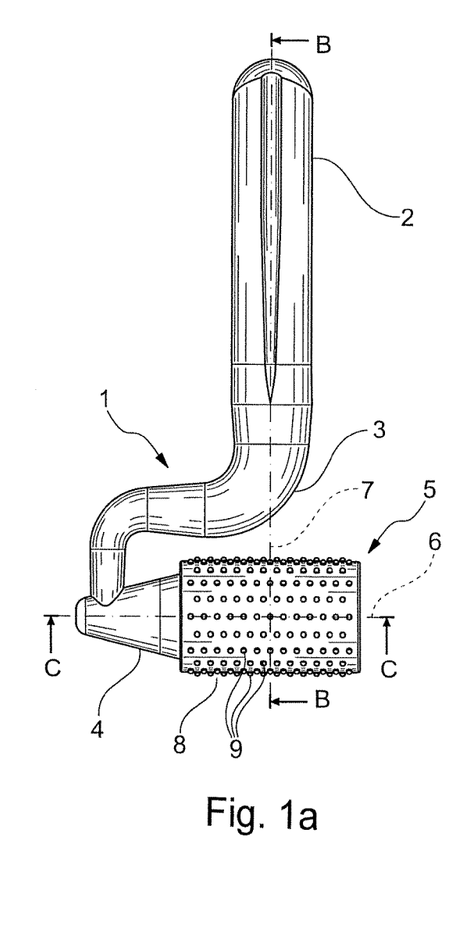
FIGS. 1a, 1b, and 1c are three different views of an embodiment of a plasma-treatment instrument with a rotatably supported roller.
Figure 1B:
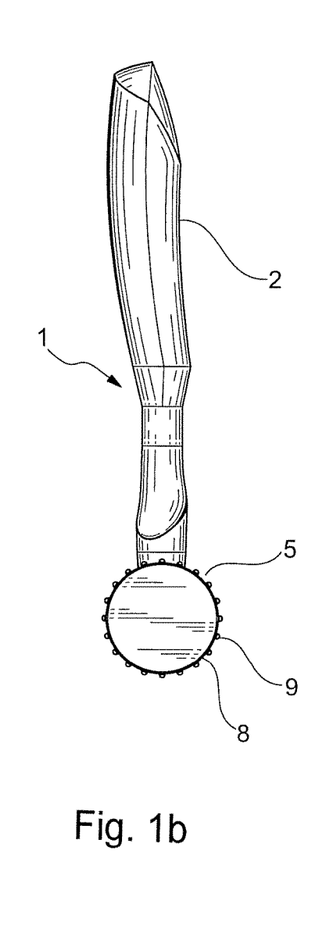
Figure 1C:
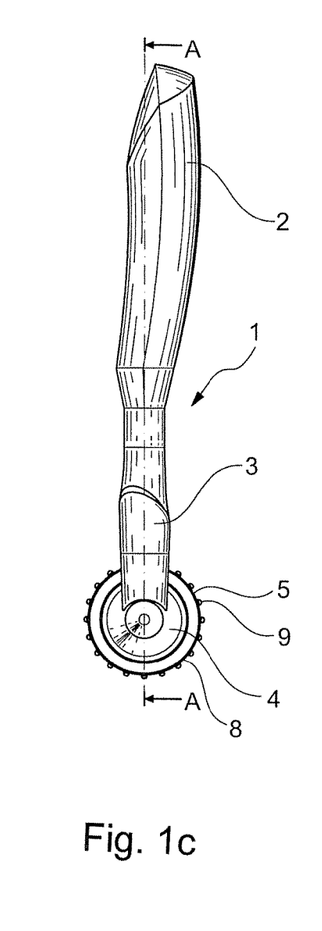

FIG. 1a shows a top view and FIGS. 1b and 1c are two side views of an embodiment of a plasma-treatment instrument. The plasma-treatment instrument exhibits a grip housing 1 which has been formed with a hollow, ergonomically shaped grip 2, with a transition piece 3, S-shaped in top view, and with a bearing section 4. A cylindrical roller 5 is rotatably supported on one side on the bearing section 4. The cylindrical roller 5 is capable of rotating about an axis of rotation 6, the location of which in FIG. 1a) corresponds to section line C-C which has been drawn in. The axis of rotation 6 is perpendicular to a longitudinal axis 7 of the grip 2, which coincides with section line B-B in FIG. 1a) The cylindrical roller 5 exhibits a circular cylindrical cross-section and a shell surface 8 on which numerous elevations 9 are located. The elevations 9 are burled and exhibit between themselves a clear spacing which corresponds to at least the largest dimension of the burled elevations 9 in top view.

Figure 2:
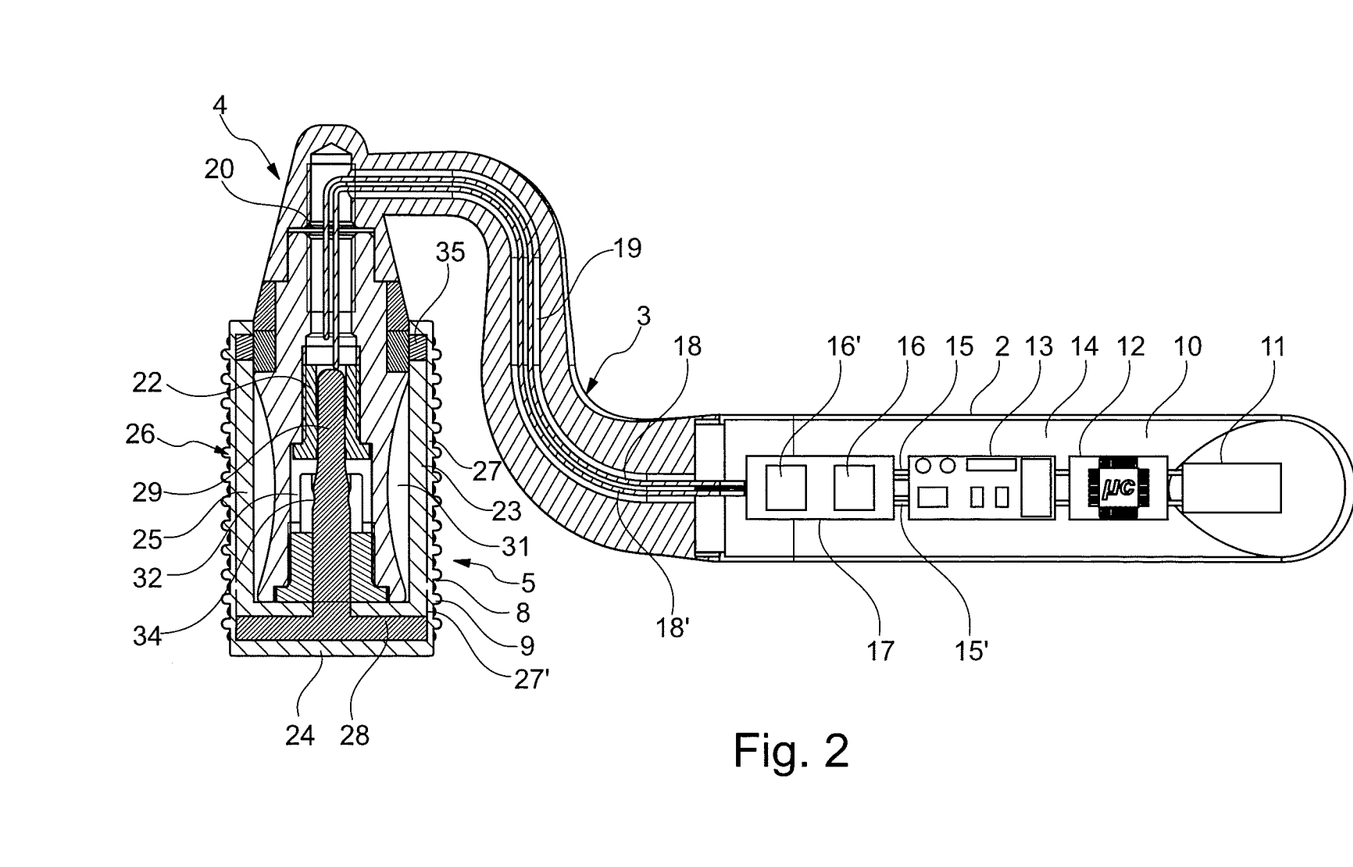
FIG. 2 is a longitudinal section along section line A-A in FIG. 1c)

The longitudinal section, represented in FIG. 2, along section line A-A in FIG. 1c) illustrates the basic internal structure of the treatment instrument. In a hollow space 10 of the grip 2 a battery compartment 11 is located, in which rechargeable or non-rechargeable batteries are located. In the case of rechargeable batteries, the grip 2 may have been designed to be plugged onto a charging station such as is known from other hand-held instruments such as, for instance, toothbrushes, dental water-jets or the like. The batteries from the battery compartment 11 supply a microprocessor 12 which, together with an electronics module 13, forms a controller 14. The controller 14 serves for generating trigger pulses at two outputs 15, 15' of the electronics module 13. The trigger pulses are of equal magnitude but of differing polarity in relation to a reference potential. The two trigger pulses are respectively applied to a coil 16, 16' of a high-voltage stage 17, in which the trigger pulses are transformed into high-voltage pulse trains with rapidly declining amplitude. The two pulse trains are of opposite polarity and of equal magnitude, so that the voltages add up to a substantially constant reference potential, in particular a ground potential. The pulse trains form partial a.c. voltages which are conducted through a duct 19 in the transition piece 3 into the bearing section 4 on a respective high-voltage line 18, 18'. For the purpose of ensuring an insulation of the two high-voltage conductors 18, 18' from one another, the duct has preferentially been filled out with an insulating material introduced in liquid form and cured.

Figure 3:
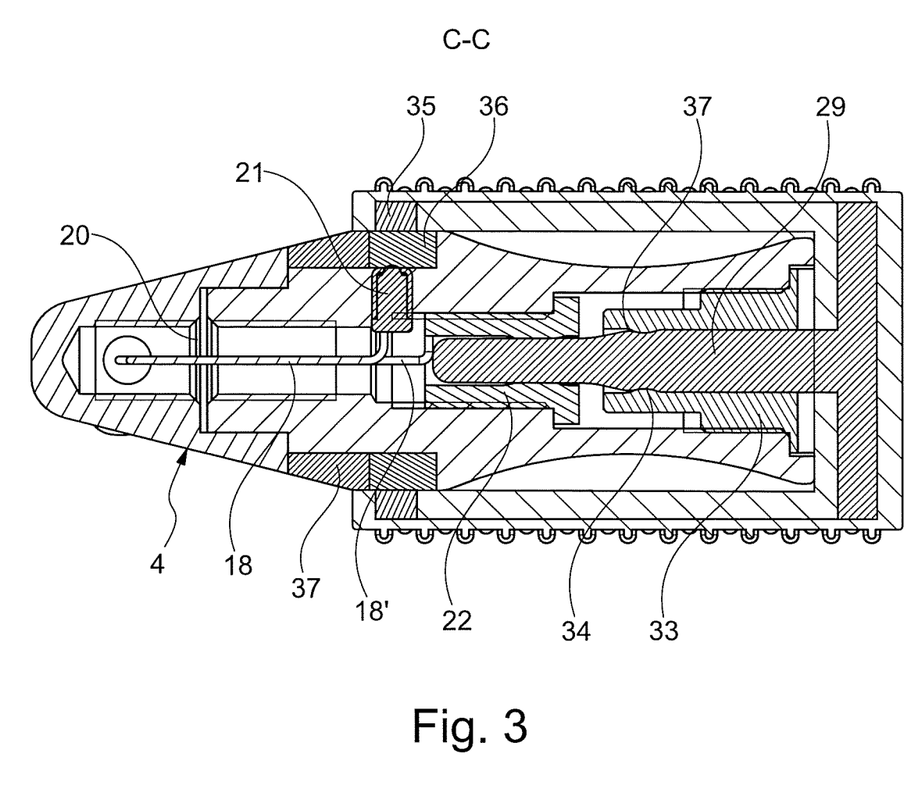
FIG. 3 is a section through the treatment instrument and axially through the roller along section line C-C in FIG. 1a)

In the bearing section 4 the high-voltage conductors 18, 18' extend parallel to one another through two appropriate bores of an inserted guide piece 20, and terminate at a radially oriented contact piece 21, on the one hand, and at a central, axially directed contact sleeve 22, on the other hand, as can best be discerned in FIG. 3.

The roller 5 takes the form of a hollow pot with a circular cylindrical shell wall 23 which on one side, namely at the end of the roller 5 facing away from the bearing section 4, has been sealed off with a front wall 24. The front wall 24 has been produced in one piece with the shell wall 23 and consists of a dielectric 25. The dielectric has, for instance, been produced in an injection-molding process and encloses on all sides an electrode 26 which has been formed from a first partial electrode 27 and from a second partial electrode 27'. The partial electrodes 27, 27' are arranged into the shell wall 23 at a fixed and equal spacing from the shell surface 8. Into the front wall 24 a massive contact end-piece 28 has been embedded which is adjoined centrally and in one piece by an axial bolt 29 which protrudes into the contact sleeve 22. The pot-like configuration of the roller 5 brings about an internal space 31 of the roller 5, into which an inner piece 30 protrudes which has been formed as part of the bearing section 4. In the assembled state, the inner piece 30 abuts the front wall 4 with an end face. The inner piece 30 exhibits an elongated internal space 32, the inside diameter of which tapers repeatedly in stepwise manner, proceeding from the front wall 24, and after each of the taperings has been endowed with a thread. The contact sleeve 22, which surrounds the free end of the contact bolt 29 in contacting manner, has been screwed into a section having a small diameter. At the end of the inner piece 30 that points toward the front wall 24 a guide bushing 33 has been screwed into the internal space 32 of the inner piece 30. The inner piece 30 is a stationary part of the bearing section 4. The roller 5 is rotatably fastened to the bearing section via a latching joint 34 between the guide bushing 33 and the bolt 29, and is able to rotate about the inner piece 30. At the end of the roller 5 pointing toward the bearing section 4 a contact ring 35 inserted into the dielectric 25 is located, which is adjoined by the first partial electrode 27. The second partial electrode 27', on the other hand, adjoins the contact end-piece 28.

FIG. 3 allows it to be discerned that an intermediate contact ring 36 has been inserted into the inner piece 30 between the contact piece 21, connected to the high-voltage conductor 18, and the contact ring 35. In alignment with the intermediate contact ring 36, the bearing section 4 exhibits a stationary insulating terminating ring 37, on which the last piece of the shell wall 23 of the roller 5 slides in the course of rolling along. The contact ring 35 forms a clamp joint with the intermediate contact ring 36, so that the intermediate contact ring 36 on the inner piece 30 is able to rotate in rotary connection with the contact ring 35. The representation of section B-B (FIG. 1)) illustrates that the guide bushing 33 exhibits in the region of the latching joint 34 a central longitudinal section, by virtue of which two guide legs 33' have been formed, between which the bolt 29 fits in with a bulge 37, accompanied by spreading of the guide legs 33'.

Figure 4:
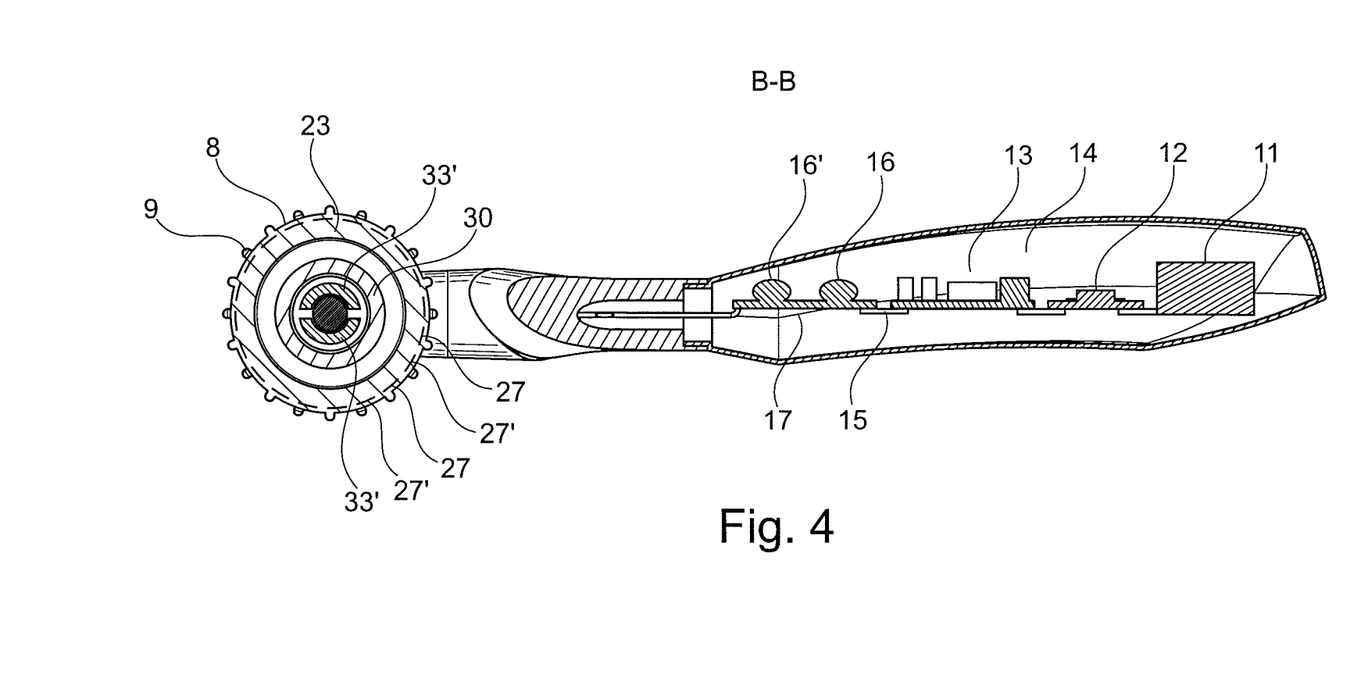
FIG. 4 is a longitudinal section along section line B-B in FIG. 1a)

FIG. 4 further allows it to be discerned that sections of the first partial electrode 27 and of the second partial electrode 27' adjoin one another in alternating manner over the periphery in the axial direction of the roller 5 and in each instance exhibit a dielectric strip 38 between themselves.

Figure 5:
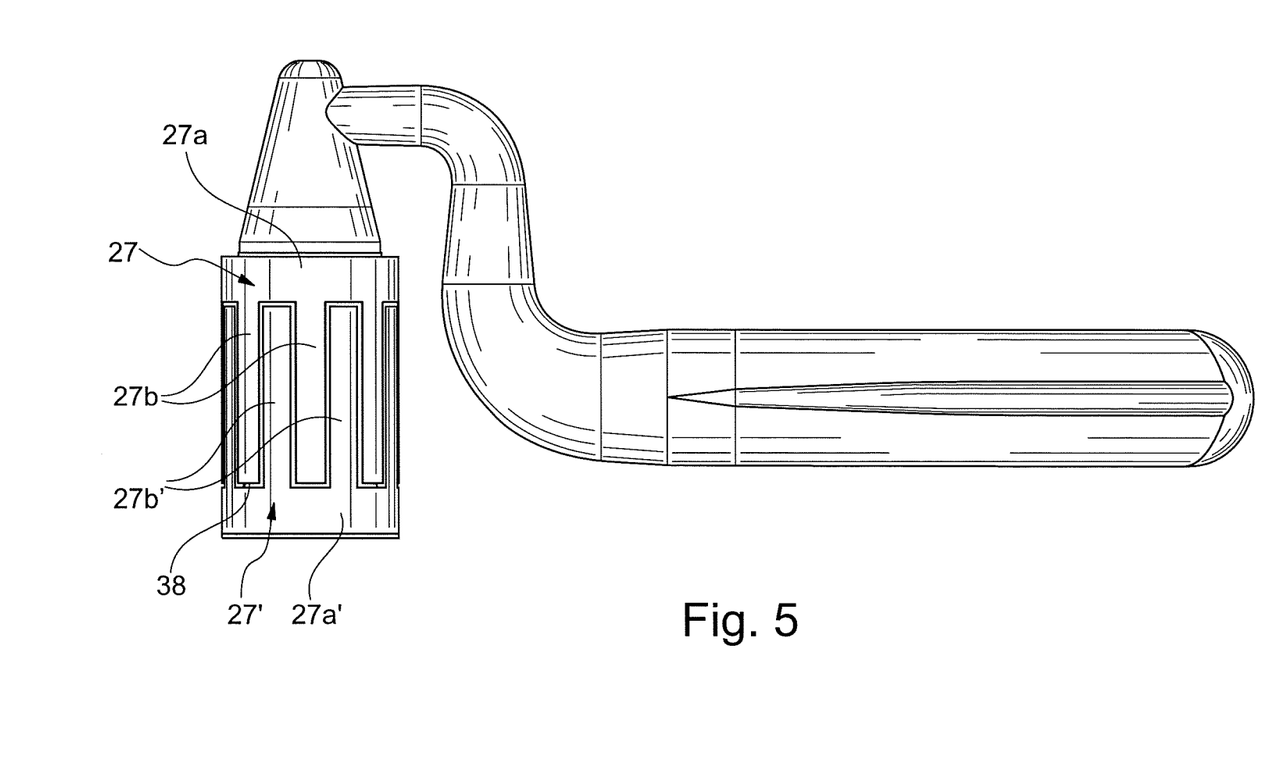
FIG. 5 is a view according to FIG. 1a) with a schematic representation of the electrode arrangement formed from two partial electrodes on the shell surface of the roller.
Figure 6:
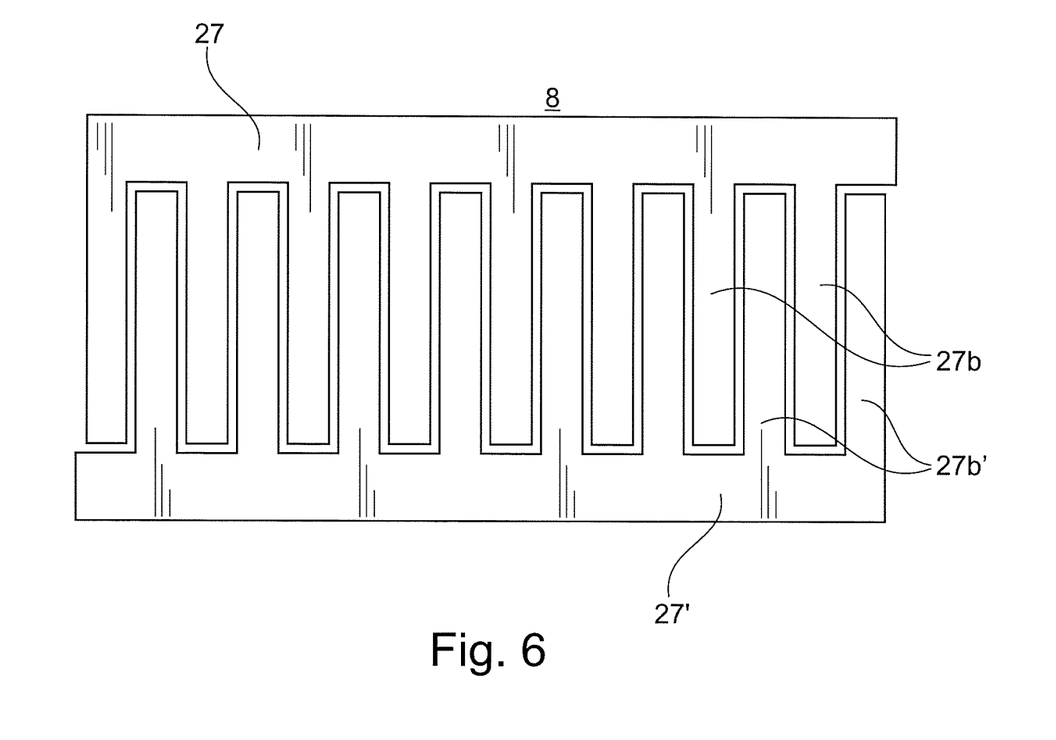
FIG. 6 is a schematic representation of the development of the shell surface at the level of the electrode arrangement.

The representations shown in FIGS. 5 and 6 illustrate the design of the first partial electrode 27 and of the second partial electrode 27', which respectively exhibit a marginal section 27a, 27a' and, proceeding therefrom, axially directed sections 27b, 27b' which engage one another in comb-like manner from the two sides. In this way, the dielectric strip 38 insulating the two partial electrodes 27, 27' from one another arises in the meandering shape discernible in FIGS. 5 and 6. This design of the partial electrodes 27, 27' has the effect, over the predominant length of the roller 5, that sections 27b and 27b' adjoin one another at short intervals in the roll-along direction of the roller 5, as a result of which an intense electric near field arises, in which the plasma forms, but at an already short distance the overlapping electric fields compensate and therefore are not perceptible for the environment.

FIG. 6 illustrates the development of the shell surface 8 represented in FIG. 5 at the level of the partial electrodes 27, 27'.

The invention claimed is:

1. A plasma-treatment instrument for treating a surface with a dielectric-barrier plasma field which is generated between an electrode, supplied with a high alternating current (a.c.) voltage by a controller, and the surface,
    wherein the electrode forms with a dielectric surrounding the electrode a cylindrical roller,
    wherein the cylindrical roller is rotatably supported in a grip housing with a shell surface, and is configured to be rolled along the surface,
    wherein the electrode comprises at least two partial electrodes arranged alongside one another at equal intervals from the shell surface, wherein the at least two partial electrodes are insulated from one another by the dielectric, wherein the at least two partial electrodes are connected or connectable to different terminals of a source of high a.c. voltage,
    wherein adjacent partial electrodes of the at least two partial electrodes are fed by the controller with equal-but-opposite, with respect to the waveform and the voltage level, partial a.c. voltages compensating each other.

2. The plasma-treatment instrument according to claim 1, wherein the at least two partial electrodes each have strip-like sections which are arranged alongside one another, extending parallel to one another.

3. The plasma-treatment instrument according to claim 2, wherein the strip-like sections extend in an axial direction of the roller.

4. The plasma-treatment instrument according to claim 1, wherein the partial electrodes from different axial marginal sections are arranged in an alternating manner relative to one another in a circumferential direction with different sections extending axially in comb-like manner, and wherein the partial electrodes are insulated from one another by a meandering dielectric strip.

* * * * *